United States Patent [19]
Meitzler et al.

[11] Patent Number: 5,301,542
[45] Date of Patent: Apr. 12, 1994

[54] FLEXIBLE FUEL PI FILTER SENSOR

[75] Inventors: Allen H. Meitzler, Ann Arbor; George S. Saloka, Dearborn, both of Mich.

[73] Assignee: Ford Motor Company, Dearborn, Mich.

[21] Appl. No.: 78,783

[22] Filed: Jun. 17, 1993

Related U.S. Application Data

[63] Continuation of Ser. No. 834,890, Feb. 11, 1992, abandoned.

[51] Int. Cl.⁵ .................. G01N 27/22; G01R 27/26
[52] U.S. Cl. ........................... 73/61.43; 73/61.44; 73/61.41; 324/672; 324/663; 324/690
[58] Field of Search ............... 73/61.43, 61.44, 61.41; 324/605, 608, 658, 663, 664, 665, 672, 679, 688, 690

[56] References Cited

U.S. PATENT DOCUMENTS

| | | |
|---|---|---|
| 3,238,453 | 3/1966 | Henry et al. |
| 4,438,749 | 3/1984 | Schwippert |
| 4,453,125 | 6/1984 | Kimura |
| 4,594,968 | 6/1986 | Degobert et al. |
| 4,706,630 | 11/1987 | Wineland et al. |
| 4,770,129 | 9/1988 | Miyata et al. |
| 4,905,655 | 3/1990 | Maekawa |
| 4,909,225 | 3/1990 | Gonze et al. |
| 4,915,084 | 4/1990 | Gonze |
| 4,939,467 | 7/1990 | Nogami et al. |
| 4,945,863 | 8/1990 | Schmitz et al. |
| 4,971,015 | 11/1990 | Gonze |
| 4,974,552 | 12/1990 | Sickafus |
| 5,103,184 | 4/1992 | Kapsokavathis ............... 73/61.44 |
| 5,231,358 | 7/1993 | Kapsokavathis ............... 73/61.43 |

OTHER PUBLICATIONS

Wiszler, "Automatic Control of Internal Combustion Engines Operating on Gasoline/Alcohol Mixtures by Means of Electronic Systems" a doctoral dissertation presented to the faculty of Heidelberg University, Germany, Jul., 1983.

"Information and Data on Alcohol Sensor", Japan Electronic Control Systems Co., Ltd. (1988).

"Methanol Sensor", distributed by Japan Electronic Control Systems Co., Ltd. at SAE Convergence Meeting, Oct., 1990.

*Primary Examiner*—Kenneth A. Wieder
*Assistant Examiner*—Jose M. Solis
*Attorney, Agent, or Firm*—Allan Lippa; Roger L. May

[57] ABSTRACT

A flexible fuel dielectric-effect sensor is disclosed wherein three capacitors, immersed in the fuel flow, are connected to define a pi filter.

25 Claims, 2 Drawing Sheets

FLEXIBLE FUEL PI FILTER SENSOR

This application is a continuation application of Ser. No. 07/834,890, filed Feb. 11, 1992, now abandoned.

BACKGROUND OF THE INVENTION

The present invention relates generally to a flexible fuel system for determining a fuel mixture and more particularly to a dielectric-effect sensor for such a system.

Dielectric-effect sensors have been under investigation for several years. Two such sensors are shown in U.S. Pat. Nos. 4,915,034 and 4,939,467, and the teachings thereof are incorporated herein by reference. A similar sensor is described in a doctoral dissertation entitled "Automatic Control of Internal Combustion Engines Operating on Gasoline/Alcohol Mixture by Means of Electronic Systems," submitted by G. Wiszler in July 1983 to Heidelberg University, Heidelberg, Germany. The teachings thereof are also incorporated by reference.

SUMMARY OF THE INVENTION

In a principal aspect, the present invention is a dielectric-effect sensor for use in a flexible fuel system, such as a gasoline/alcohol system. The system utilizes a capacitance within the sensor and dependent upon the fuel mixture, e.g.. the percentage by weight of one fuel, to regulate certain engine parameters.

The sensor includes three separate capacitors, exposed to the fuel blend, connected in a "pi" configuration. This arrangement facilitates measurement of the fuel mixture by providing an enhanced output signal variation over the spectrum of fuel mixtures from substantially pure gasoline to substantially pure alcohol. The sensor provides an output signal variation, or discrimination ratio, in the range of twenty to fifty.

It is thus an object of the present invention to provide a dielectric-effect flexible fuel sensor. Another object is to provide a long-life, yet inexpensive dielectric-effect sensor for a flexible fuel system. Still another object is a dielectric-effect sensor wherein the discrimination ratio is substantially improved over known dielectric-effect sensors.

These and other features, objects and advantages of the present invention are set forth or implicit in the following detailed description.

BRIEF DESCRIPTION OF THE DRAWING

Preferred embodiments of the present invention are described, in detail, with reference to the drawing wherein.

FIG. is a schematic representation of a flexible fuel vehicle incorporating a preferred embodiment of the present invention.

DETAILED DESCRIPTION OF PREFERRED EMBODIMENTS

Figure 1:
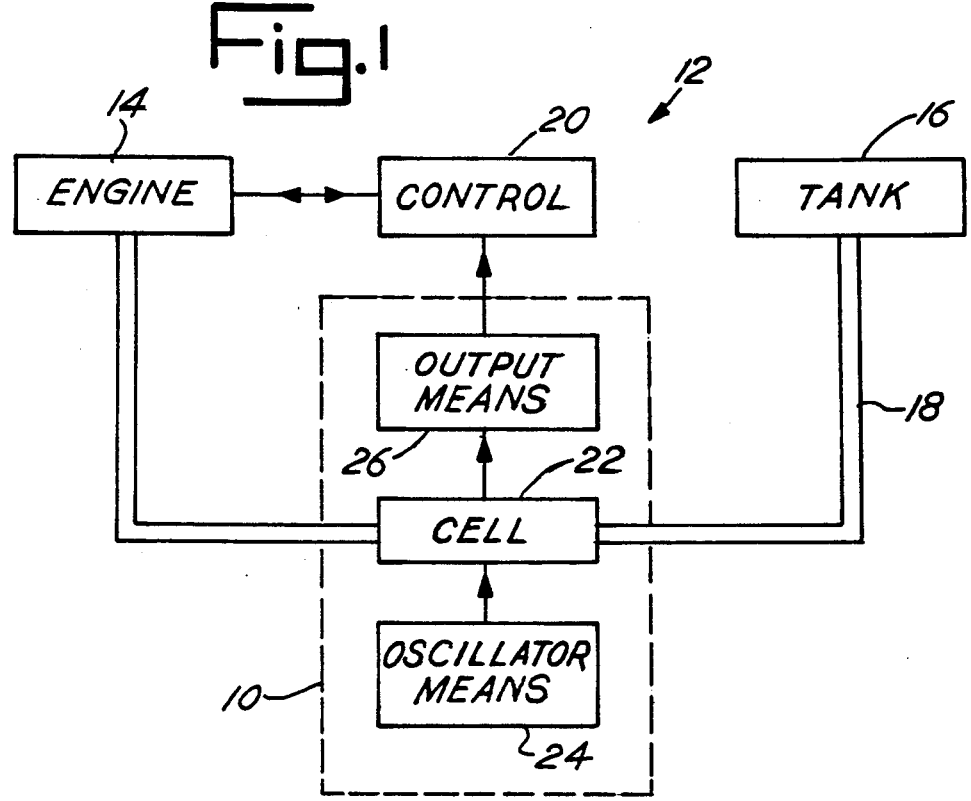
Figure 2:
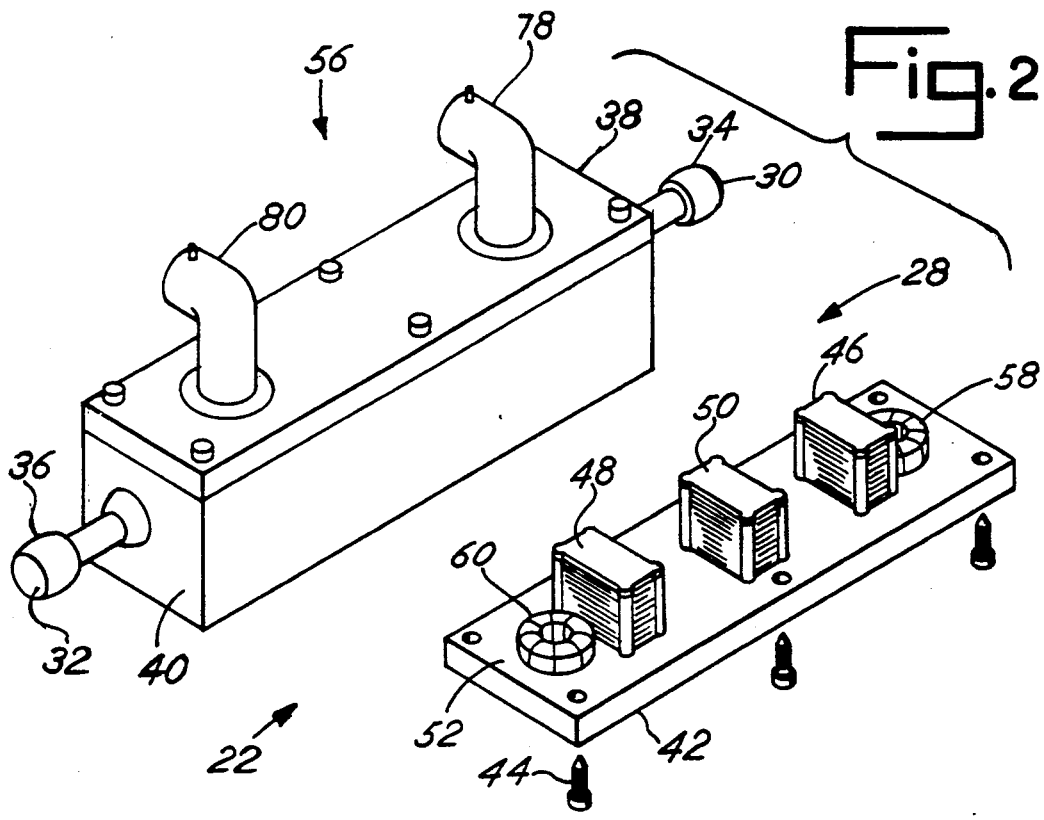
FIG. 2 is a partial, exploded perspective view of the sensor cell shown in FIG. 1.
Figure 3:
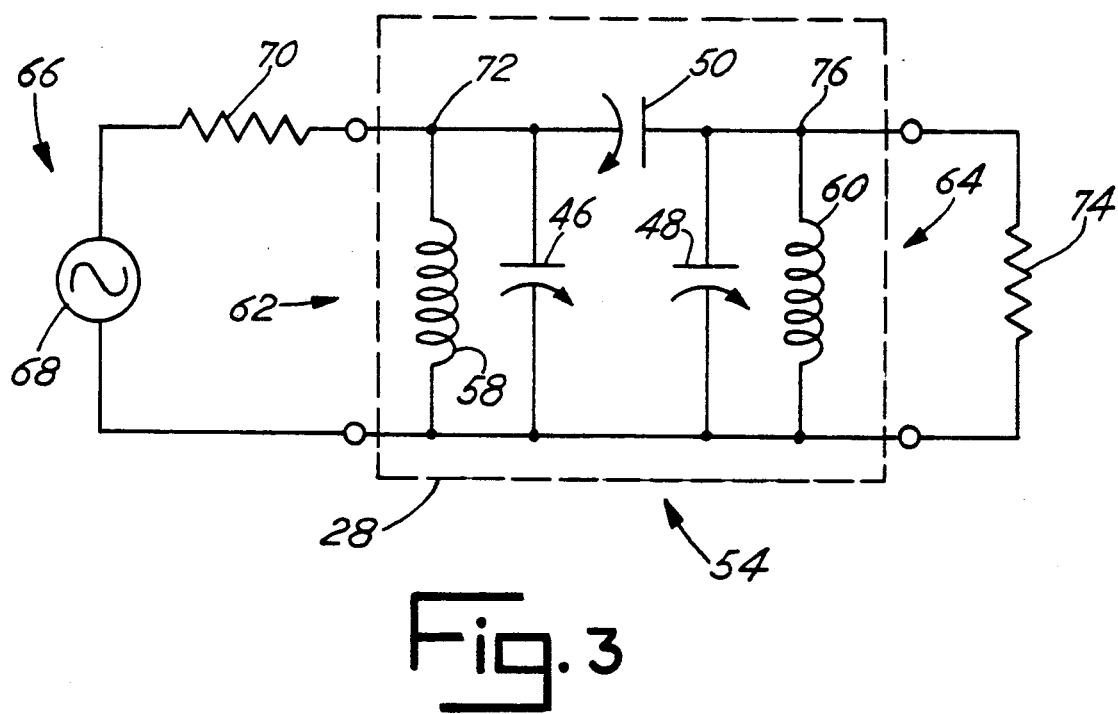
FIG. 3 is an electrical schematic of the sensor shown in FIG. 1.

Preferred embodiments of the present invention are shown in FIGS. 1-3, wherein common reference numerals are utilized. Referring thereto, the present invention is shown as a flexible fuel system, generally designated 20, for a flexible fuel vehicle 12 having an engine 14, fuel tank 16, fuel line 18 and electronic engine control 20. As is well known, the engine control 20 regulates certain parameters of engine performance based upon the fuel mixture delivered through the fuel line 18. In this preferred embodiment, a mixture of two liquid fuels, i.e., gasoline and methanol, is used, and the fuel mixture is specified by the weight percentage, of one liquid fuel, preferably methanol.

The flexible fuel system 10 includes a flexible fuel sensor 22, oscillator means 24 and output means 26. In this preferred embodiment, the sensor 22 is incorporated into the fuel line 18 to receive at least a portion of the liquid fuel mixture therein.

The sensor 22 includes a housing 28 adaptive to receive the fuel blend. The housing 28 includes a fuel inlet 30 and a fuel outlet 32, defined by inlet and outlet fuel line connectors 34, 36 respectively. The connectors 34, 36 are sealingly received by the fuel line 18 of the vehicle 12. The housing 28 is preferably brass and substantially rectangular. The connectors 34, 36 extend from respective end plates 38, 40 thereof.

A side plate 42 of the housing 28 is removably secured by screws 44. First, second and third capacitors 46, 48, 50, respectively, are secured to an interior surface 52 of the side plate 42 and rest within the housing 28 in the assembled state. The capacitors 46, 48, 50 are parallel plate capacitors having substantially the same design and the fuel blend passes between the plates thereof as it flows from the fuel inlet 30 to the fuel outlet 32 of the housing 28. As is well known, the capacitance exhibited by each capacitor 46, 48, 50 will vary with the fuel mixture.

The capacitors 46, 48, 50 are connected as a pi filter, generally designated 54. That is, the first and second capacitors 46, 48 are connected by the third capacitor 50. Opposite this connection, the first and second capacitors 46, 48 are connected to ground.

The flexible fuel sensor 22 further includes connector means, generally designated 56, secured to and extending through the housing 28, opposite the side plate 42. The connector means 56 provides a connection with the pi filter 54, external to the housing 28.

The sensor 22 also includes first and second inductors 58, 60, connected to the pi filter 54. As shown in FIG. 2, the inductors 58, 60 are mounted on the interior surface 52 of the side plate 42 to facilitate assembly. Alternatively, the inductors 58, 60 may be external to the housing 28, for example, incorporated into the oscillator means 64 and the output means 26, respectively.

The first inductor 58 is connected in parallel with the first capacitor 46 to provide an inlet tuned circuit, generally designated 62. The second inductor 60 is similarly connected across the second capacitor 48 to define an outlet tuned circuit 64. The third capacitor couples the inlet and outlet tuned circuits 62, 64. The inductors 58, 60 may also be tunable to provide an adjustment capability.

In this preferred embodiment, the capacitors 46, 48, are twenty (20) picofarads (pF) in air, representing approximately forty-two picofarads (42 pF) in gasoline and approximately six hundred fifty-six picofarads (656 pF) in methanol. The resonant frequency of the inlet and outlet tuned circuits 62, 64 is approximately two (2.0) megahertz (MHz) for methanol, and the first and second inductors 58, 60 are approximately six and three-quarters (6.75) microhenries ($\mu H$).

As best shown in FIG. 3, the sensor 22 includes an alternating current voltage source 66, such as a fixed frequency oscillator 68 having an internal impedance represented by a resistor 70. The oscillator 68 is connected to the pi filter 54 at a node 72 interconnecting the first and third capacitors 46, 50 and the first inductor 54, via the connector means 56. The sensor 22 responsively provides a control signal utilized by the electronic engine control 20. In this preferred embodiment, the control signal is the voltage developed across an output resistor 74, connected to the pi filter 54 via the connector means 56. The resistor 74 is connected to a node 76, interconnecting the second and third capacitors 48, 50 and the second inductor 60.

As best shown in FIG. 2, the connector means 56 includes drive and output coaxial terminals 78, 80. These terminals 70, 80 are connected to the nodes 72, 76, respectively.

The flexible fuel system 10 provides a normalized discrimination ratio, i.e., $V_{OUT}/V_{IN}$, in the range of fifteen to thirty. This is to be compared with a discrimination ratio for a single capacitor dielectric-effect sensor, such as shown in U.S. Pat. No. 4,915,034, of less than five. The output of the system 10 is also substantially linear.

The enhanced discrimination ratio is derived from the pi filter 54. The output voltage therefrom decreases as the fuel changes from methanol to gasoline because the value of the capacitor 50 decreases. This capacitance decrease causes an increase in its reactance and a larger voltage drop, thereby decreasing in voltage across the output resistor 74. The control signal also decreases as the fuel changes from methanol to gasoline because the capacitors 46, 48 decrease, shifting the resonant frequencies of the inlet and outlet tuned circuits 62, 64 to higher frequencies.

The inductors 58, 60 compensate for uncontrolled system capacitance (such as the stray capacitances of the input and output and the shunt capacitance of the sensor 22 itself), which reduce the effective range of signal variation. With adjustable inductors 58, 60, the transmission characteristic of the pi filter 54 can be precisely tuned and substantially maximized.

Preferred embodiments of the present invention have been described herein. It is to be understood, however, that modifications and changes can be made without departing from the true scope and spirit of the present invention as set forth in the following claims, to be interpreted in accordance with the foregoing.

What is claimed is:

1. A sensor for use in determining a fuel mixture of a flexible fuel including at least tow liquid fuels comprising, in combination:
    a housing, including a fuel inlet and a fuel outlet, for receiving said liquid fuels;
    first, second and third capacitors, within said housing and interconnected as a pi filter in communication with said flexible fuel, said third capacitor interconnecting said first and second capacitors to define said pi filter; and
    connector means, extending through said housing for providing an external connection to said pi filter.

2. A sensor as claimed in claim 1 further comprising a first inductor connected in parallel with said first capacitor to provide an inlet tuned circuit having an inlet resonant frequency.

3. A sensor as claimed in claim 2 further comprising a second inductor connected in parallel with said second capacitor to provide an outlet tuned circuit having an outlet resonant frequency.

4. A sensor as claimed in claim 3 wherein said third capacitor couples said inlet and outlet tuned circuits.

5. A sensor as claimed in claim 4 wherein said inlet and outlet resonant frequencies are substantially equal.

6. A sensor as claimed in claim 5 wherein said first and second inductors are tunable.

7. A sensor as claimed in claim 5 wherein said first, second and third capacitors are parallel plate capacitors.

8. A sensor as claimed in claim 7 wherein said first, second and third capacitors are secured to said housing.

9. A sensor as claimed in claim 8 wherein said first and second inductors are secured within said housing.

10. A fuel sensor for use in determining a fuel mixture of at least two liquid fuels comprising, in combination:
    a housing including a fuel inlet for receiving said liquid fuel and a fuel outlet for passing said liquid fuels;
    a first capacitor secured within said housing;
    a second capacitor secured within said housing; and
    a third capacitor secured within said housing and interconnecting said first and second capacitors to form a pi filter.

11. A fuel sensor as claimed in claim 10 further comprising a first capacitor to provide an inlet tuned circuit having an inlet resonant frequency.

12. A fuel sensor as claimed in claim 11 further comprising a second inductor connected in parallel with said second capacitor to provide an outlet tuned circuit having an outlet resonant frequency.

13. A fuel sensor as claimed in claim 12 wherein said inlet and outlet resonant frequencies are substantially equal.

14. A fuel sensor as claimed in claim 13 wherein said first and second inductors are tunable.

15. A fuel sensor for use in determining a fuel mixture of at least two liquid fuels comprising, in combination:
    a housing to receive said liquid fuels;
    an inlet tuned circuit, secured within said housing, having an inlet resonant frequency and a first capacitor;
    an outlet tuned circuit, secured within said housing, having an outlet resonant frequency and a second capacitor;
    a third capacitor coupled to said first and second capacitors to define a pi filter in communication within said liquid fuels; and
    connector means for coupling an external connection to said pi filter.

16. A fuel sensor as claimed in claim 15 wherein said inlet and outlet resonant frequencies are substantially equal.

17. A fuel sensor as claimed in claim 16 wherein said inlet tuned circuit and second outlet tuned circuit include first and second tunable inductors, respectively.

18. A sensor for use in determining a fuel mixture of a flexible fuel including at least two liquid fuels comprising, in combination:
    a housing including a fuel inlet for receiving said liquid fuels and a fuel outlet for passing said liquid fuels;
    a first capacitor secured within said housing;
    a second capacitor secured within said housing; and
    a third capacitor secured within said housing and interconnecting said first and second capacitors to from a pi filter in communication with said flexible fuel.

19. A sensor as claimed in claim 18 further comprising a first inductor connected in parallel with said first capacitor to provide an inlet tuned circuit having a inlet resonant frequency.

20. A sensor as claimed in claim 19 further comprising a second inductor connected in parallel with said second capacitor to provide an outlet tuned circuit having an outlet resonant frequency.

21. A sensor as claimed in claim 20 wherein said inlet and outlet resonant frequencies are substantially equal.

22. A sensor as claimed in claim 21 wherein said first and second inductors are tunable.

23. A sensor for use in determining a fuel mixture of a flexible fuel including at least two fuels comprising, in combination:

a housing including a fuel inlet and a fuel outlet to receive and pass, respectively, said liquid fuels;

an inlet tuned circuit, secured within said housing, having an inlet resonant frequency and a first capacitor;

an outlet tuned circuit, secured within said housing, having an outlet resonant frequency and a second capacitor;

a third capacitor coupled to said first and second capacitors to define a pi filter in communication within said liquid fuels; and connector means for coupling an external connection to said pi filter.

24. A sensor as claimed in claim 23 wherein said inlet and outlet resonant frequencies are substantially equal.

25. A sensor as claimed in claim 24 wherein said inlet tuned circuit and second outlet tuned circuit include first and second tunable inductors, respectively.

* * * * *